(12) United States Patent
Reu et al.

(10) Patent No.: US 9,861,374 B2
(45) Date of Patent: Jan. 9, 2018

(54) MEDICAL INSTRUMENTATION AND IMPLANTATION SET

(71) Applicant: Aesculap AG, Tuttlingen (DE)

(72) Inventors: Gerhard Reu, Tuttlingen (DE); Uwe Bader, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 83 days.

(21) Appl. No.: 14/970,980

(22) Filed: Dec. 16, 2015

(65) Prior Publication Data

US 2016/0175109 A1 Jun. 23, 2016

(30) Foreign Application Priority Data

Dec. 18, 2014 (DE) .................. 10 2014 119 083

(51) Int. Cl.
| | | |
|---|---|---|
| *A61F 2/36* | (2006.01) | |
| *A61B 17/16* | (2006.01) | |
| *A61F 2/30* | (2006.01) | |
| *A61B 90/92* | (2016.01) | |

(52) U.S. Cl.
CPC ...... *A61B 17/1668* (2013.01); *A61B 17/1659* (2013.01); *A61B 90/92* (2016.02); *A61F 2/30744* (2013.01); *A61F 2/36* (2013.01); *A61F 2002/30616* (2013.01); *A61F 2002/30617* (2013.01); *A61F 2002/30713* (2013.01)

(58) Field of Classification Search
CPC .......... A61F 2/3859; A61F 2/38; A61F 2/367; A61F 2/30965; A61B 17/1659; A61B 17/1668

See application file for complete search history.

(56) References Cited

U.S. PATENT DOCUMENTS

| | | | |
|---|---|---|---|
| 4,671,275 | A | 6/1987 | Deyerle |
| 5,019,108 | A | 5/1991 | Bertin et al. |
| 5,766,261 | A | 6/1998 | Neal et al. |
| 6,224,605 | B1 | 5/2001 | Anderson et al. |
| 2002/0133233 | A1* | 9/2002 | Blamey .............. A61B 17/1668 623/23.18 |
| 2012/0259338 | A1 | 10/2012 | Carr et al. |
| 2014/0276850 | A1 | 9/2014 | Chaney et al. |

FOREIGN PATENT DOCUMENTS

| | | |
|---|---|---|
| DE | 29816064 | 12/1998 |
| DE | 102008020199 | 10/2009 |
| EP | 2027833 | 2/2009 |
| WO | 96/17553 | 6/1996 |

* cited by examiner

*Primary Examiner* — Jason-Dennis Stewart
(74) *Attorney, Agent, or Firm* — Lipsitz & McAllister, LLC

(57) ABSTRACT

Medical instrumentation is provided, in particular for implanting a hip joint stem, which includes a rasping instrument having a rasp stem defining a longitudinal direction. The rasp stem has at least two depth stops arranged or formed thereon. An implantation set is also provided which includes such a rasping instrument.

20 Claims, 6 Drawing Sheets

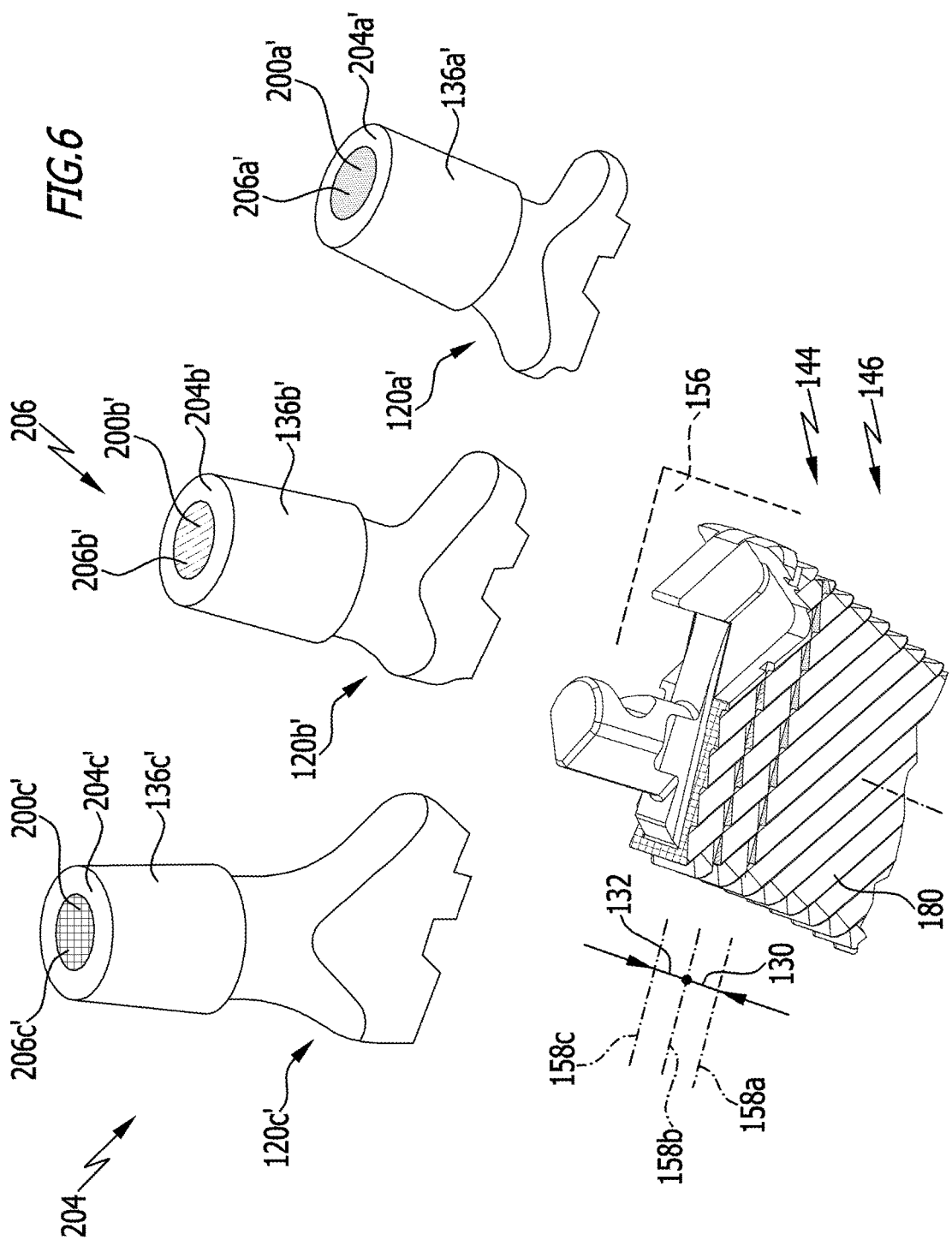

MEDICAL INSTRUMENTATION AND IMPLANTATION SET

CROSS-REFERENCE TO RELATED APPLICATIONS

This application claims the benefit of German patent application number 10 2014 119 083.1 filed on Dec. 18, 2014, which is incorporated by reference herein in its entirety and for all purposes.

FIELD OF THE INVENTION

The present invention relates to medical instrumentation generally, and more specifically to medical instrumentation, in particular for implanting a hip joint stem, comprising a rasping instrument having a rasp stem defining a longitudinal direction.

The present invention further relates to implantation sets generally, and more specifically to an implantation set comprising a modular implant set, including at least two different implant parts, and medical instrumentation.

BACKGROUND OF THE INVENTION

Artificial hip joints, which are known as hip joint endoprostheses, are often used to treat patients whose hip joints show excessive signs of wear and tear. Other indications are conditions that are known as coxa vara and coxa valga. Coxa vara, that is to say an "outward curvature of the hip", describes the condition where the angle known as the CCD angle (centrum-collum-diaphyseal angle), that is the angle formed between the femoral neck and the shaft of the femur bone, is less than 120°. When the CCD angle is about 125°, this is referred to as a "normal hip", or coxa norma. The opposite condition of coxa vara is coxa valga, which often occurs in young children and newborns and represents an increase in the CCD angle beyond 135°. The deviations from the norm result from growth—coxa valga situations are normal in newborns—and pathological changes. For example, coxa vara often develops in elderly persons. However, there is also wide variation in the geometries of the proximal femoral area based on national differences.

In endoprosthetic hip joint replacement different medial contours of the femoral canal, different angles of the femoral neck, and associated therewith also the resulting positions of the head centre point of the hip joint endoprostheses are of particular importance. In order to enable appropriate treatment of these three above-described classes of coxa valga, coxa norma and coxa vara, secure fixation of the implant in the femoral canal needs to be ensured. In this regard and depending on how the implant is fixed in the femoral canal, medial contact of the prosthesis stem with the cortical bone of the femur is very important. Therefore, an implant system is always optimized for one of the three groups mentioned and cannot be used at all or only under exceptional conditions in caring for the other groups. Furthermore, what is also characteristic of the three groups mentioned is the position of the rotational centre of the joint. Compared with a standard femur, a valgus femur has rather a small offset and a varus femur has rather a large offset. This range and in particular the interplay between specific medial contact and position of the head centre point cannot be covered with the usual systems.

One problem which exists with the implantation of the different hip joint endoprostheses is that extensive instrumentations are required depending on the patient's pathological situation.

SUMMARY OF THE INVENTION

In a first aspect of the invention, medical instrumentation, in particular for implanting a hip joint stem, comprises a rasping instrument having a rasp stem defining a longitudinal direction. The rasp stem has at least two depth stops arranged or formed thereon.

In a second aspect of the invention, an implantation set comprises a modular implant set, including at least two different implant parts, and medical instrumentation, in particular for implanting a hip joint stem. Said medical instrumentation comprises a rasping instrument having a rasp stem defining a longitudinal direction. The rasp stem has at least two depth stops arranged or formed thereon.

BRIEF DESCRIPTION OF THE DRAWINGS

The foregoing summary and the following description may be better understood in conjunction with the drawing figures, of which:

FIG. 6 is a schematic representation of partial views of further exemplary embodiments of hip stems for the indications of coxa valga, coxa norma and coxa vara with the rasp stem as shown in the partial view of FIG. 4.

DETAILED DESCRIPTION OF THE INVENTION

Figure 1A:
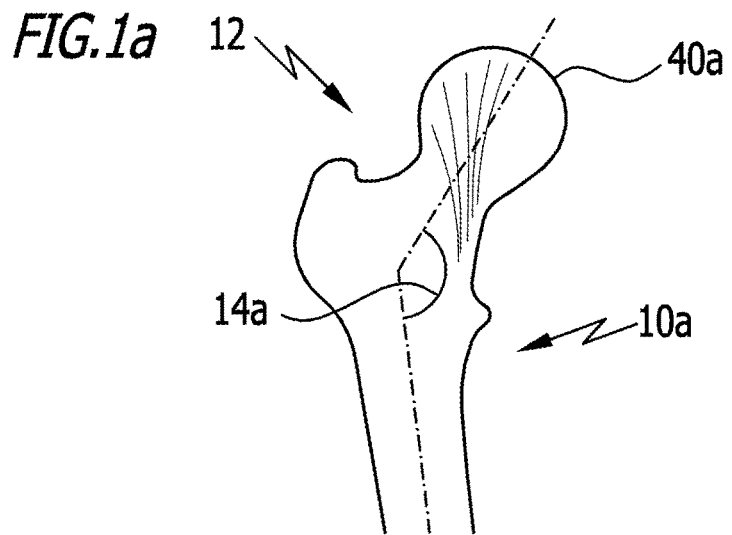
FIG. 1a is a schematic representation of coxa valga.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to medical instrumentation, in particular for implanting a hip joint stem, comprising a rasping instrument having a rasp stem defining a longitudinal direction, wherein the rasp stem has at least two depth stops arranged or formed thereon.

Instrumentation configured in such a way enables the preparation of femur bones of patients who exhibit different pathological conditions at the hip for implantation of a hip joint stem with the use of just a single rasping instrument.

For example, construction of the medial geometry of the prosthesis stems can be realized via an arc that has the same radius for all of the three variants of prosthesis stems designed to treat coxa vara, coxa norma and coxa valgus. However, despite the same radius, different medial contact is created based on the different heights of the centre of circle of the stem arc. If the remaining geometry of the prosthesis stem below a resection line is identical for all of the three variants, then the implant bed can in principle be prepared using the same rasping instrument for all of the three types of prosthesis stems. The only prerequisite is that the rasp stem be impacted into the femoral canal deeper or not so deep by an amount that is equal to the value by which the centre points of the medial radii of the prosthesis stems are offset to each other; this can be, for example, 5 mm deeper or 5 mm less deep. In order to ensure that the rasp stem is struck in only deep enough that the prosthesis stem to be implanted in each case makes optimal contact with the femur on the medial side, the rasp stem has at least two depth stops arranged or formed thereon. These enable, for example, an impaction depth to be limited or an indication to be given to the surgeon as to how deep he or she has already impacted the rasp stem into the femoral canal. Providing the at least two depth stops on the rasp stem enables in particular at least two, preferably three different prosthesis stems to be implanted in an optimal manner with the use of just a single rasping instrument.

Preferably, an end face of the rasp stem pointing in a proximal direction comprises the at least one depth stop face. Said end face may optionally have further elements projecting therefrom, such as a coupling element for connecting the rasp stem to a handle or the like. The end face thereby forms a depth stop that can provide an indication to the surgeon of how deep the rasp stem has already been driven into the femur bone.

It is advantageous for the at least two depth stops to be arranged or formed in spaced-apart relationship to each other. In this way, different depths of impaction can be predetermined for or indicated to the surgeon.

A particularly simple configuration of the instrumentation can be achieved if at least one of the at least two depth stops comprises at least one groove. For example, a groove can be easily shaped on an outer side of the rasp stem by milling or other material-removing machining processes.

Advantageously, at least two of the at least two depth stops comprise at least one groove. For example, two grooves and the end face can form a total of three depth stops. Furthermore, each depth stop can also comprise two or more grooves. For example in a rasp stem shaped rectangularly in cross-section, there can be formed for each depth stop a total of up to four grooves on four outer faces; these can together form an annular groove in particular, and they together define one single depth stop.

It is advantageous for the at least one groove on the rasp stem to extend parallel or essentially parallel to an end face of the rasp stem pointing in a proximal direction or to extend transversely, in particular perpendicularly, to the longitudinal direction. For example, if the end face itself defines a depth stop, grooves can be formed parallel or essentially parallel to the end face in the manner described, thus providing a simple way of indicating to a surgeon a distance to the end face.

Advantageously, the at least one groove is spaced apart from the end face. Thus, by way of a distance between the end face and the at least one groove, a different depth of impaction of the rasp stem can be predetermined for or indicated to a surgeon.

A particularly simple configuration of the instrumentation can be achieved if the at least one groove defines a groove longitudinal direction and/or extends in a straight line or in an essentially straight line. Furthermore, this configuration facilitates the use of the instrumentation by the surgeon, in particular because he or she can safely identify a depth of impaction by comparing a position of the visible groove to a proximal end of the prepared femur bone.

In order for a surgeon to be able to clearly identify the at least two depth stops even during a surgical procedure, it is advantageous for the at least one groove to be formed on a side face of the rasp stem that points in a direction transversely to the longitudinal direction.

In accordance with another preferred embodiment of the invention, provision may be made for the at least one groove to comprise at least one groove side face and for the at least one groove side face to define the at least one depth stop face. For example, a groove can also comprise two, three or more groove side faces depending on the cross-sectional shape of the groove. In particular, the groove can be configured in the shape of a wedge having two groove side faces or in the shape of a rectangle having three groove side faces.

In order for a surgeon to be able to clearly identify the depth of impaction of a rasp stem, it is advantageous for the at least one groove side face to extend parallel or essentially parallel to the end face.

It is advantageous for the depth stop faces defined by the at least two depth stops to have different surface textures or to be differently coloured. Colours in particular are a simple means of enabling a surgeon to distinguish easily between the at least two depth stop faces. The surgeon can thereby safely identify how far the rasp stem has already been driven into the femur bone and whether it may need to be driven in still further.

In accordance with a further preferred embodiment of the invention, provision may be made for the at least two depth stops to be coloured with an individual identification colour in each case and for the identification colour to be either blue or green or orange. In particular, three depth stops can be coloured in one of the three colours in each case, said colours allowing for unambiguous distinction between the three depth stops. In particular, the depth stop faces as well can be coloured with the identification colour in the manner described.

Advantageously, three depth stops are provided. Three depth stops enable implantation of corresponding prosthesis stems for the treatment of patients with coxa vara, coxa norma and coxa valga with the use of only a single rasping instrument. This reduces the number of instruments that need to be carried in inventory and, therefore, material and processing costs.

The manipulation of the instrumentation is further simplified if each of the at least two depth stops comprises at least one depth stop face. A depth stop can comprise one, two or more depth stop faces. These preferably mark the same depth of impaction for the rasp stem.

Advantageously, at least one of the at least two depth stops comprises two depth stop faces. For example, the two depth stop faces can be arranged such that they are arranged or formed on different sides of the rasp stem. This provides a simple and safe way for the rasping instrument to be used for implanting hip stems for both a patient's left and right hip joint.

It is advantageous for the two depth stop faces of the at least one of the at least two depth stops to be arranged or formed separately from each other. In this way, for instance, they are capable of being arranged or formed in a clearly identifiable manner on the rasp stem on two different sides thereof that point away from each other.

Manufacture of the instrumentation is simplified in particular by the at least one depth stop face being planar or essentially planar. Moreover, a planar depth stop face is particularly clearly identifiable to a surgeon so that he or she can impact the rasp stem into the femur bone only as deep as needed.

In order to improve the distinguishability of the at least two depth stops for the surgeon, it is advantageous for the depth stop faces of the at least two depth stops to be of different widths.

Advantageously, the proximal-most depth stop face is the widest. It is thus still clearly identifiable even when the rasp stem is impacted into the femur bone to maximum depth.

It is advantageous for the distal-most depth stop face to be wider than an intermediate depth stop face interposed between the distal-most and the proximal-most depth stop face. In this way, the depth stops can be distinctly distinguished even when they lie relatively close together.

In order to safely mark a different depth of impaction on the rasp stem, it is advantageous for the at least one depth stop face of one of the at least two depth stops to be spaced apart from the at least one depth stop face of another one of the at least two depth stops relative to the longitudinal direction.

In accordance with a further preferred embodiment of the invention, provision may be made for the at least one depth stop face of one of the at least two depth stops to extend parallel or essentially parallel to the at least one depth stop face of another one of the at least two depth stops. Depth stop faces that extend parallel to each other are particularly clearly identifiable by a surgeon as depth stops.

It is advantageous for the rasp stem to have end face portions pointing in a proximal direction, said end face portions forming or comprising the depth stop faces. In particular, the depth stop faces can be arranged or formed pointing in a proximal direction or in an essentially proximal direction. Thus, they are clearly identifiable by a surgeon even when the rasp stem is impacted into the femur bone.

Preferably, the rasp stem comprises three, four, five or more end face portions. For example, two end face portions can comprise a depth stop face in each case, which together form a depth stop.

The rasp stem is particularly simple to manufacture if at least two depth stop faces define depth stop face planes which extend transversely, in particular perpendicularly, to the longitudinal direction.

Advantageously, the rasp stem is of symmetrical or essentially symmetrical configuration with respect to a plane of symmetry which runs transversely, in particular perpendicularly, to at least one of the depth stop faces. Furthermore, the plane of symmetry can contain a longitudinal axis of the rasp stem. This configuration simplifies the construction of the rasp stem. In addition, the ease of manipulation thereof is improved because the depth stop faces are equally well identifiable by the surgeon in both the preparation of a left femur and the preparation of a right femur.

Advantageously, the rasp stem comprises three depth stop faces which are arranged or formed in equidistant or essentially equidistant relation with respect to the longitudinal direction. Such a configuration is particularly advantageous if the prosthesis stems for the treatment of coxa valga, coxa norma and coxa vara have equidistant medial centres of curvature.

It is further advantageous for the instrumentation to have a coupling element arranged or formed on the rasp stem for coupling the rasp stem with a handle element. It is thereby possible, by way of the handle element, which preferably has an impact face for impacting the rasp stem into the femur, to impact the rasp stem in place and then separate the rasp stem and the handle element from each other in order for example to mount a prosthesis neck with a joint head to the rasp stem in order to determine the orientation and position of the joint head. This is advantageous in order to then determine optimal prosthesis size as well as neck length and joint ball diameter.

The handle element can be coupled with the rasp stem in a particularly simple manner if the coupling element is arranged or formed pointing in a proximal or in an essentially proximal direction. In particular, the coupling element can be configured in the form of a coupling projection or also in the form of a coupling recess.

It is advantageous for a proximal coupling element end face of the coupling element to contact or to be arranged distally of the most proximally extending depth stop face plane. With this configuration, it is possible that after release of the handle element, it is the proximal-most depth stop face in particular that is the element that projects the farthest from the rasp stem in a proximal direction. Thus, the depth stop is clearly identifiable and the coupling element is arranged or formed in the least interfering way.

In accordance with another preferred embodiment of the invention, provision may be made for a coupling element longitudinal axis of the coupling element and at least one of the depth stop face planes to enclose an angle that is less than 90°. In particular, said angle is in a range of 50° to 80°. Choosing the angle to be in the range indicated is in particular advantageous in that it allows the coupling element to be temporarily connected to a trial neck with a trial joint head, which will then point in the desired direction.

The construction of the instrumentation is further simplified if the coupling element longitudinal axis runs parallel to or lies in the plane of symmetry.

In order to simplify manufacture of the instrumentation further, it is advantageous for the rasp stem to have two side faces pointing away from each other. In particular, these can be of planar or essentially planar form. Furthermore, they can carry cutting elements, such as rasping teeth or rasping grooves which allow work to be performed on a cavity of the femur bone.

Advantageously, the two side faces extend parallel or essentially parallel to the plane of symmetry. In this way, the cavity of the femur bone can be prepared in a particularly compact manner for the reception of the prosthesis stem of the hip joint endoprosthesis.

In order to make the depth of impaction of the rasp stem particularly clearly identifiable to a surgeon, it is advantageous for one of the depth stop faces to adjoin at least one of the two side faces. This is preferably the distal-most depth stop face.

The distal-most depth stop is particularly clearly identifiable by a surgeon if the distal-most depth stop face plane extends transversely, in particular perpendicularly, with respect to a side face plane defined by one of the two side faces.

The ease of manipulation of the medical instrumentation can be improved if it comprises a handle element for coupling with the coupling element. The handle element can have, in particular on the proximal end thereof, an impact face for an impact tool in order to impact the rasp stem into the bone cavity of the femur.

It is further advantageous for the instrumentation to comprise an impact tool. With this, the rasp stem can be impacted into the femoral bone cavity in a simple and safe manner.

The present invention further relates to an implantation set, comprising a modular implant set, including at least two different implant parts, and medical instrumentation, in particular for implanting a hip joint stem. Said medical instrumentation comprising a rasping instrument having a rasp stem defining a longitudinal direction, wherein the rasp stem has at least two depth stops arranged or formed thereon.

In particular, the implantation set proposed in accordance with the invention enables, with the use of just one single rasping instrument, a bone cavity of a femur bone to be prepared for the implantation of different implant parts, in particular for the implantation of different prosthesis stems for the treatment of different indications.

It is further advantageous for the at least two different implant parts each to comprise an identification element and for the identification elements of the at least two different implant parts to be different from each other. The identification elements allow a surgeon and the surgeon's support staff to make a safe selection between different implant parts, for example prosthesis stems for the treatment of coxa vara, coxa norma and coxa valga, said selection being executed specifically and properly from a set of implant parts provided, said implant parts forming the implant set.

Preferably, the identification elements of the at least two different implant parts are different from each other in respect of their colour schemes, on the basis of their surface textures and/or by their positions on the at least one implant part. This provides a simple way for a surgeon to distinguish between the different implant parts, for example on the basis of their respective colour schemes or their surface textures or depending on a location or position in which they are arranged or formed on the implant part.

Surgeon-selected implant parts can be implanted particularly safely if each identification element of the at least two different implant parts is associated with one of the at least two depth stops. For example, when a surgeon selects for implantation an implant part having an individually formed identification element, then he or she will know immediately which one of the at least two depth stops on the rasp stem corresponds to the implant part selected and, therefore, how far he or she must impact the rasp stem into the bone.

Associating implant parts with depth stops can be accomplished in a particularly simple and safe manner if a colouring of the at least two depth stops corresponds to a colouring of the identification elements of the at least two different implant parts. In other words, colours that are the same belong together. When a surgeon selects an implant part, he or she can immediately identify which particular depth stop on the rasp stem corresponds to the implant part selected. With this, the surgeon also knows how far he or she needs drive the rasp stem into the bone.

In particular, it is advantageous for the identification elements of the at least two different implant parts to be coloured with the same identification colours as those of the depth stops. Thus, with knowledge of the identification colour of the identification element of the implant part selected, the depth stop that needs to be considered in the preparation of the femoral cavity can be determined in a simple and safe manner.

The identification elements of the at least two different implant parts can be configured in a particularly simple manner if they are configured in the form of geometrical surface portions. For example, corresponding geometrical surface portions can be formed on an outer surface of the implant part by colour or by a readily identifiable surface texture.

The identification elements can be configured in a particularly simple manner if the geometrical surface portions are formed in the shape of circular surfaces or polygons. These can be configured for example in one piece with the implant parts or applied thereto in the form of adhesive labels.

A surgeon can identify particularly clearly and quickly the type of implant part selected by him or her if the geometrical surface portions are arranged or formed on neck end faces, pointing in a proximal direction, of necks of the implant parts. These will still point in the surgeon's direction even after implantation, and the surgeon can thus recheck at the end as to whether the appropriate implant part has been used.

It is advantageous for the identification elements to be configured such that they are capable of being releasably connected to the at least two different implant parts or such that they are arranged or formed in non-releasable relationship therewith. In particular, releasably connectable identification elements have the advantage of being able to be easily removed during or after the surgical intervention. For example, they can be saved for documentation purposes in order to document the type of implant part used.

Preferably, the identification elements are configured in the form of protective caps. For example, these can be configured to be mounted or clipped onto necks of implant stems. In particular, they then serve the surgeon as an identification of the implant part and, optionally, also to protect the implant part. In particular, damage to the neck of the hip joint stem entails the danger that safe connection thereof to the ball-and-socket joint head can no longer be accomplished.

Furthermore, it is advantageous for the identification elements to be capable of being connected to the at least two different implant parts in a force locking and/or form-locking manner. In particular, this ensures that the identification elements cannot be undesirably released from the implant parts which they identify.

FIG. 1a is a schematic representation of a femur bone 10a in a setting of coxa valga 12 with a CCD angle 14a greater than 140°.

Figure 1B:
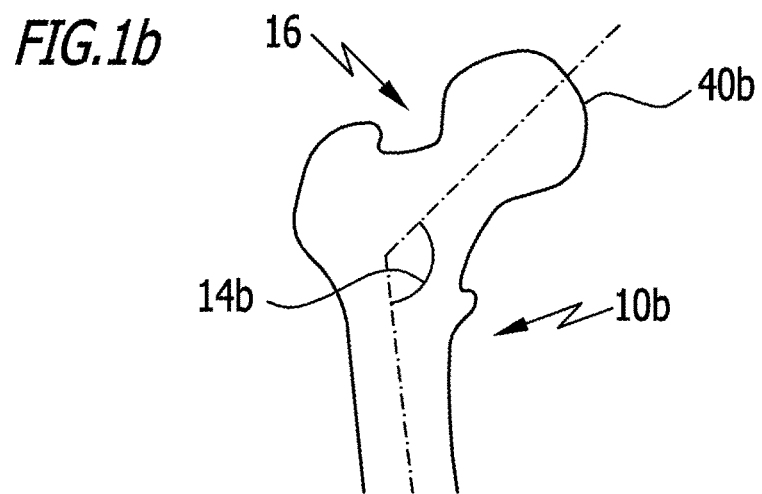
FIG. 1b is a schematic representation of coxa norma.

FIG. 1b is a schematic representation of a femur bone 10b in a setting of coxa norma 16 with a CCD angle 14b of about 125°.

Figure 1C:
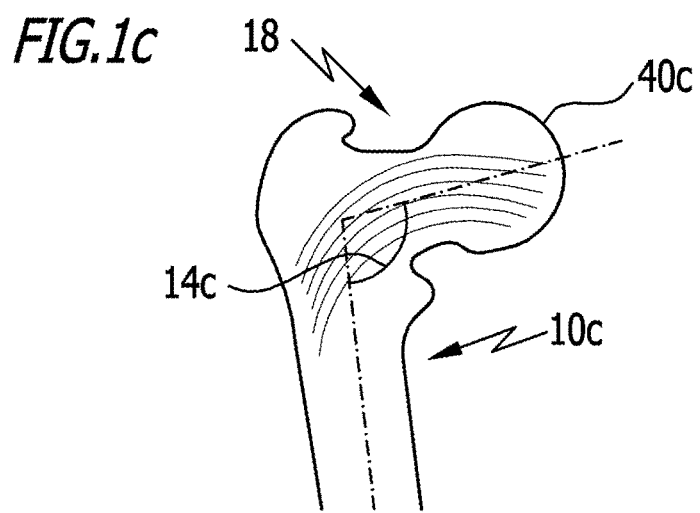
FIG. 1c is a schematic representation of coxa vara.

FIG. 1c is a schematic representation of another femur bone 10c in a setting of coxa valga 18 with a CCD angle 14c less than 120°.

Figure 2A:
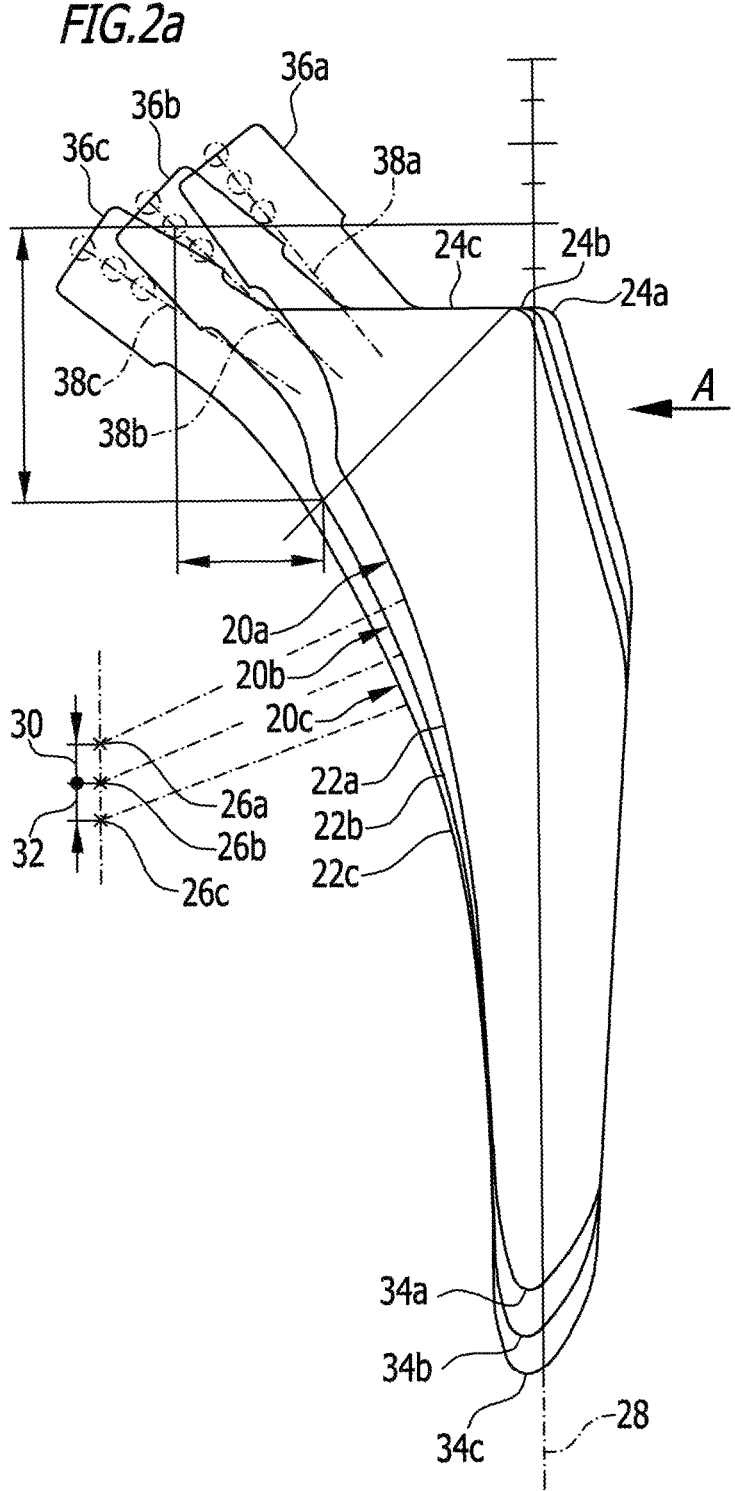
FIG. 2a is a schematic representation of superimposed contours of three hip stems for the indications of coxa valga, coxa norma and coxa vara.
Figure 2B:
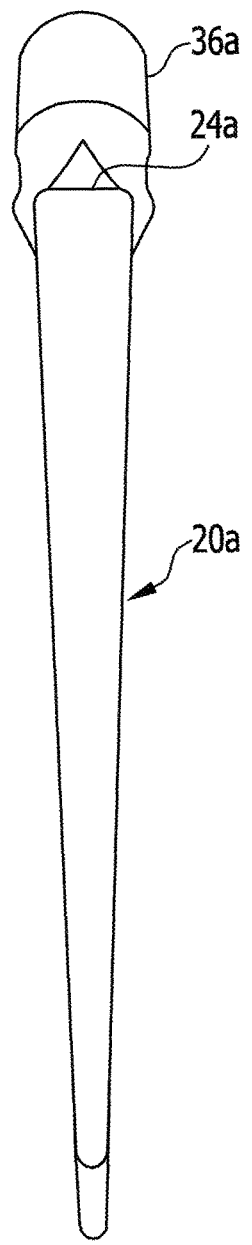
FIG. 2b is a view of the hip stem for the indication of coxa valga of FIG. 2a in the direction of the arrow A.
Figure 3:
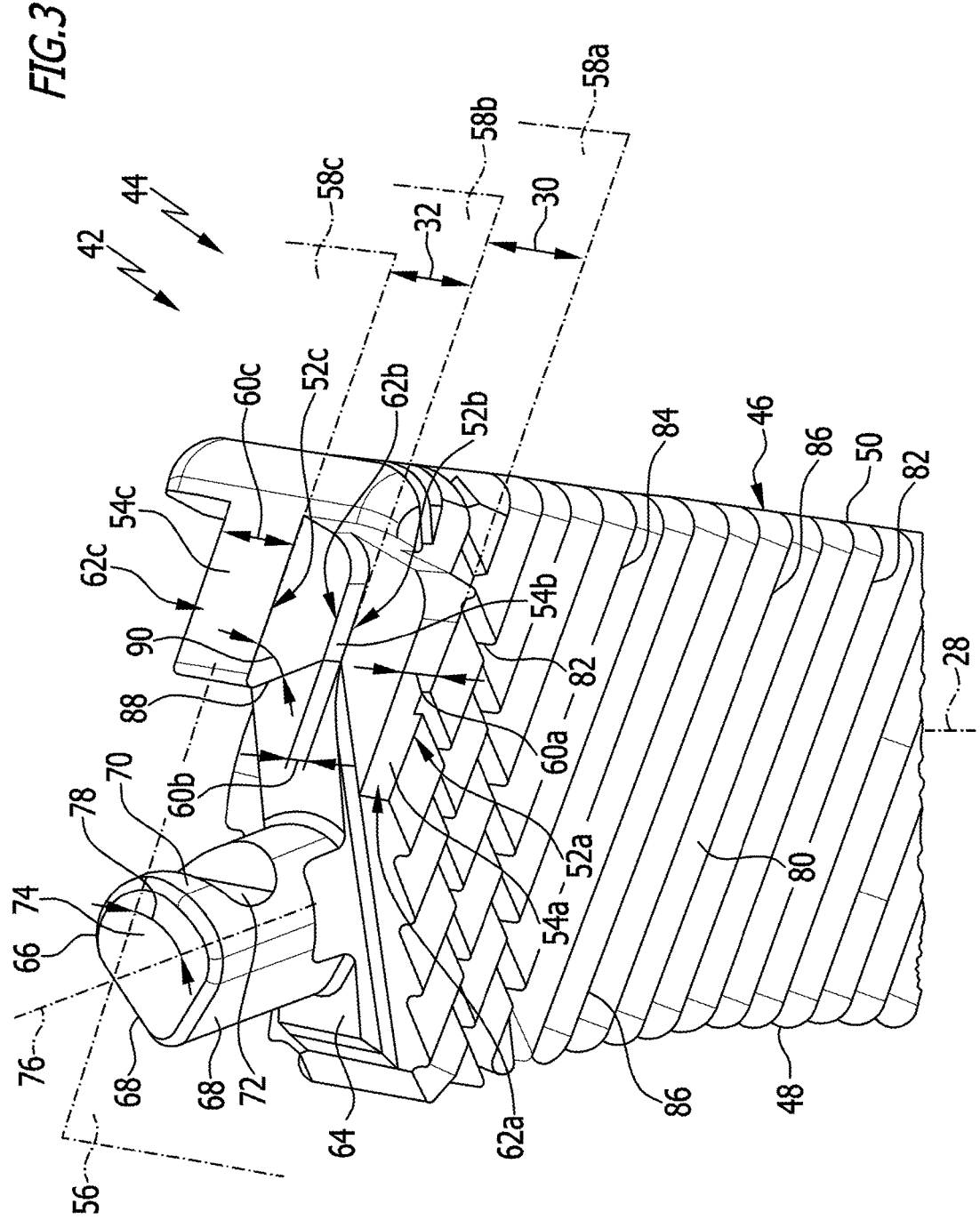
FIG. 3 is a schematic perspective partial view of a rasp stem having three depth stops.

The three contours of the prosthesis stems 20a, 20b and 20c schematically shown in FIG. 2a serve to treat the three pathological situations schematically shown in FIGS. 1a to 1c. Medial side faces 22a, 22b and 22c of the prosthesis stems 20a, 20b and 20c are concavely curved pointing away from said side faces 22a, 22b and 22c, and all of them have the same radius of curvature. If proximal end faces 24 of the prosthesis stems 20a, 20b and 20c are aligned flush with each other as exemplified for their contours in FIG. 2a, this will result in centre points 26a, 26b and 26c of contact circles which contact the side faces 22a, 22b and 22c to be offset relative to each other with respect to a longitudinal direction 28 defined by the prosthesis stems 20a, 20b and 20c, namely by a distance 30 between the centre points 26a and 26b and by a distance 32 between the centre points 26b and 26c.

As is clearly shown in FIG. 2a, a total length of the prosthesis stem 20c is larger than a total length of the prosthesis stem 20b, which in turn is larger than a total length of the prosthesis stem 20a. The smaller the CCD angle 14a, 14b and 14c, the farther distal ends 34a, 34b and 34c of the prosthesis stems 20a, 20b and 20c respectively are away from the respective end faces 24a, 24b and 24c.

Necks 36a, 36b and 36c of the prosthesis stems 20a, 20b and 20c define neck longitudinal axes 38a, 38b and 38c, each enclosing an angle with the longitudinal direction 28 that increases in size as the size of the CCD angle 14a, 14b and 14c decreases.

For the implantation of the prosthesis stems 20a, 20b and 20c, the femur bones 10a, 10b and 10c need to be partially resected by severing the femoral heads 40a, 40b and 40c. A medullary canal of the femur bones 10a, 10b and 10c is then prepared using medical instrumentation 42 comprising a rasping instrument 44. The rasping instrument 44 comprises a rasp stem 46 having a medial side face 48 formed with a radius of curvature corresponding to the radius of curvature of the side faces 22a, 22b and 22c of the prosthesis stems 20a, 20b and 20c. A lateral side face 50 of the rasp stem 46 is nearly parallel to the longitudinal direction 28.

In order that the same rasp stem 46 can be used for preparing the femur bones 10a, 10b and 10c, it must, for the preparation of the medullary cavity of the respective femur bone 10a, 10b and 10c, be impacted thereinto to different depths, where the depth increases as the CCD angle 14a, 14b and 14c respectively of the respective indication decreases. In other words, the rasp stem 46 needs to be struck in to a depth deeper by the distance 32 for the implantation of the prosthesis stem 20c for the indication of coxa vara than what is required for the indication of coxa norma. On the other hand, for the indication of coxa norma, the rasp stem 46 needs to be impacted into the femur bone 10b to a depth deeper by the distance 30 than what is required for the indication of coxa valga 12.

In order for a surgeon to be able to impact the rasp stem 46 into the respective femur bone 10a, 10b and 10c to the appropriate depth, the rasp stem has three depth stops 52a, 52b and 52c formed thereon. The depth stop 52a comprises two depth stop faces 54a, and the depth stop 52b comprises two depth stop faces 54b. The depth stop 52c comprises a single depth stop face 54c. The rasp stem 46 generally has mirror symmetry with respect to a plane of symmetry 56 containing the longitudinal direction 28.

The depth stop faces 54a, 54b and 54c define depth stop face planes 58a, 58b and 58c which extend parallel to one another. A distance between the depth stop face planes 58a and 58b corresponds to the distance 30, and a distance between the depth stop face planes 58b and 58c corresponds to the distance 32. In the prosthesis stems 20a, 20b and 20c schematically shown in the figures, the distance 30 corresponds to the distance 32. In other words, the depth stop faces 54a, 54b and 54c are formed in equidistantly spaced relationship to one another.

The depth stop faces 54a, 54b and 54c form a part of end face portions 62a, 62b and 62c pointing in a proximal direction. A width of the depth stop face 54c is larger than a width of the two depth stop faces 54a, which in turn are double the width of the depth stop faces 54b.

The proximal-most depth stop face 54c corresponds to the indication of coxa vara 18, the depth stop face 54b corresponds to the indication of coxa norma 16 and the depth stop face 54a corresponds to the indication of coxa valga 12.

A coupling end face 64 of the rasp stem 46 inclined in a medial direction relative to the depth stop faces 54b carries a coupling element 66, configured symmetrically with respect to the plane of symmetry, for coupling the rasp stem 46 to a handle element not shown in the figures. The latter can in particular have an impact face in order to impact the rasp stem 46 held by the handle element into the cavities of the femur bones 10a, 10b and 10c.

The coupling element 66 has two side faces 68 inclined to each other and pointing in a medial direction, said side faces 68 being connected together via a cylindrical surface 70 pointing in a lateral direction. Formed in the area of the cylindrical surface is a recess 72 pointing in a lateral direction. An end face 74 of the coupling element 66 pointing in a proximal direction is below the depth stop face plane 58c, i.e. fully distal thereof. A coupling element longitudinal axis 76 of the coupling element 66 is inclined in relation to the depth stop face planes 58a, 58b and 58c at an angle 78 less than 90°. The angle 78 is preferably in the range of 50° to 80°. Furthermore, the coupling element longitudinal axis 76 lies in the plane of symmetry 56.

The rasp stem 46 further comprises two side faces 80 pointing away from each other, said side faces 80 connecting together the side faces 48 and 50. The side faces 80 extend substantially parallel to each other and have mirror symmetry with respect to the plane of symmetry 56. The two side faces 80 and the side faces 48 and 50 comprise a multiplicity of grooves 82 which extend parallel to each other and have sharp edges 84 that form rasping teeth 86.

The distal-most depth stop faces 54a adjoin the side faces 80 and extend transversely, preferably perpendicularly, thereto.

The side face 50 extends in a proximal direction approximately up to the level of the depth stop face 54c. Furthermore, the depth stop faces 54b and 54a are each somewhat offset in a medial direction relative to the lateral side face 50.

The depth stop face 54c is formed on an essentially cuboid projection having a front face 88 pointing in a medial direction, said front face 88 extending essentially parallel to the coupling element longitudinal axis 76. The front face 88 encloses an angle 90 with the depth stop face 54c, the value of said angle 90 being in the range of approximately 50° to 70°, preferably 60°. Thus, the depth stop faces 54a extend farthest in a medial direction. Furthermore, the depth stop face 54c projects beyond the depth stop face 54b in a medial direction.

The three depth stops 52a, 52b and 52c allow the rasping instrument 44 to be used for preparing all of the femur bones 10a, 10b and 10c irrespective of which one of the prosthesis stems 20a, 20b and 20c is to be implanted. Depending on the prosthesis stem 20a, 20b and 20c to be implanted, the rasp stem 46 is impacted into the partially resected femur bone only far enough until the depth stop face 54a, 54b and 54c associated with the respective indication comes to lie at the same level as a resection plane of the femur bones 10a, 10b and 10c. By providing the depth stops 52a, 52b and 52c on the rasp stem 46, the provision of two further rasp stems for the two remaining indications can be dispensed with.

Figure 4:
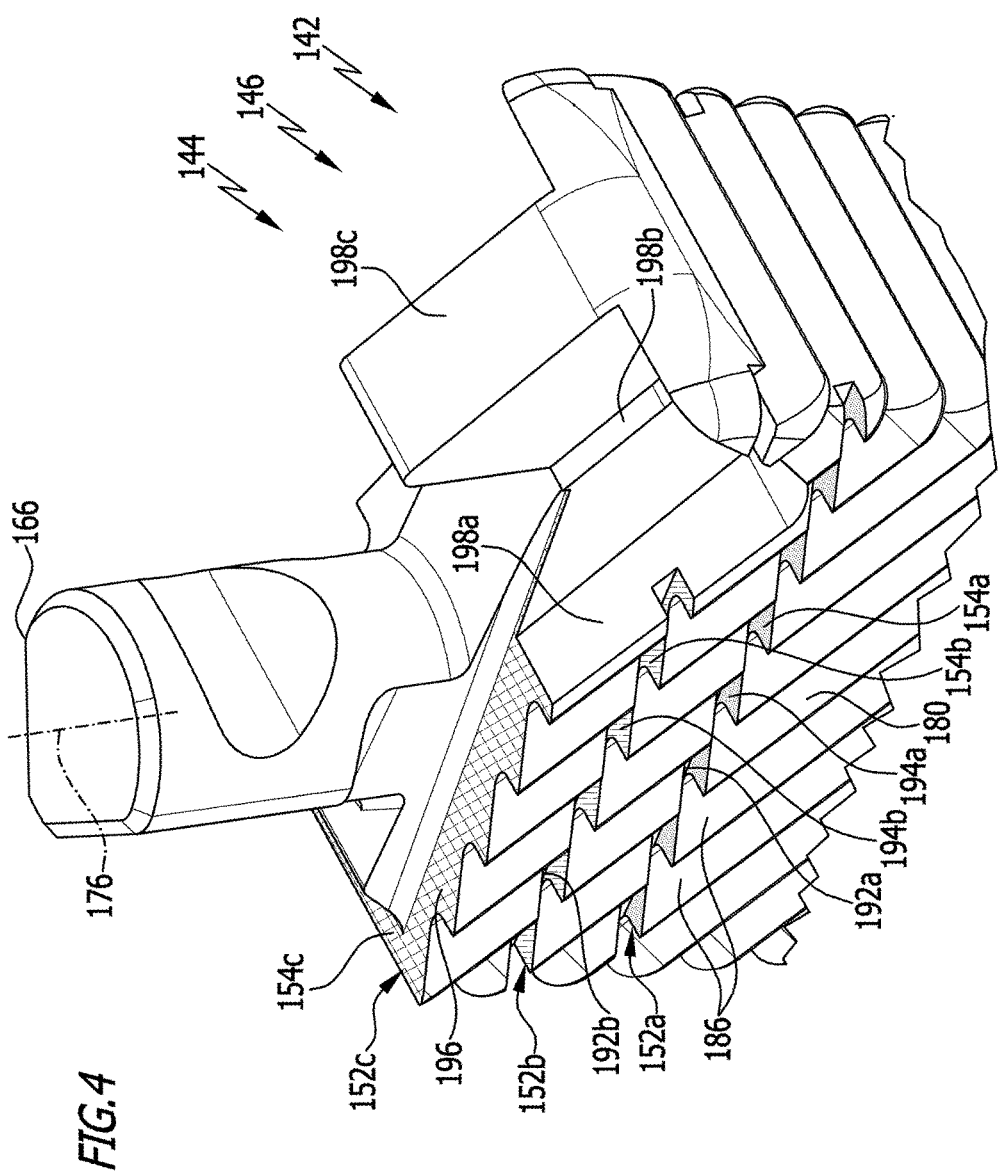
FIG. 4 is a schematic perspective partial view of another exemplary embodiment of a rasp stem having three depth stops.

FIG. 4 illustrates in partial view a further exemplary embodiment of a rasping instrument generally indicated by the reference character 144. Its basic construction is the same as that of the rasping instrument 44, and identical elements bear the same reference characters but preceded by "1" to indicate elements corresponding to the rasping instrument 144.

The rasping instrument 144 comprises a rasp stem 146 including a total of three depth stops 152a, 152b and 152c. The depth stops 152a and 152b are configured in the form of grooves 192a and 192b in the side faces 180 which extend transversely to the rasping teeth 186. Groove side faces 194a and 194b pointing in a proximal direction, i.e. in a direction towards the coupling element 166, define depth stop faces 154a and 154b. An end face 196 of the rasp stem from which the coupling element 166 extends away in a proximal direction defines the depth stop face 154c of the depth stop 152c.

The depth stop faces 154a, 154b and 154c define depth stop face planes 158a, 158b and 158c which extend parallel to one another. A distance 130 between the depth stop face plane 158a and the depth stop face plane 158b corresponds to the distance 132 between the depth stop face plane 158b and the depth stop face plane 158c. Thus, the two grooves 192a and 192b are spaced apart both from the end face 196 and from each other.

Furthermore, the depth stop face planes 158a, 158b and 158c extend transversely to the longitudinal direction 128 defined by the rasp stem 146.

The depth stop 152a corresponds to the indication of coxa valga and thus forms a corresponding impaction mark for the surgeon.

The depth stop 152b corresponds to the indication of coxa norma and forms an impaction mark corresponding thereto.

Further, the depth stop 152c defines an impaction mark for the coxa vara indication.

The faces of the rasping shaft 146 that are designated as depth stop faces 54a, 54b and 54c in the rasping shaft 46 define shoulder height faces 198a, 198b and 198c. The shoulder height face 198a corresponds to the shoulder height of the prosthesis stem 120a, the shoulder height face 198b corresponds to the shoulder height of the prosthesis stem 120b and the shoulder height face 198c corresponds to the shoulder height of the prosthesis stem 120c.

In order to make the indication that corresponds to the respective depth stop 152a, 152b and 152c easily identifiable to a surgeon, the depth stop faces 154a, 154b and 154c are coloured in different colours. This is schematically shown in FIG. 4 by different hatchings. Optionally, the depth stop faces 154a, 154b and 154c can also be provided with different surface textures that ensure ease of identification of the respective depth stops 152a, 152b and 152c by a surgeon.

Figure 5C:
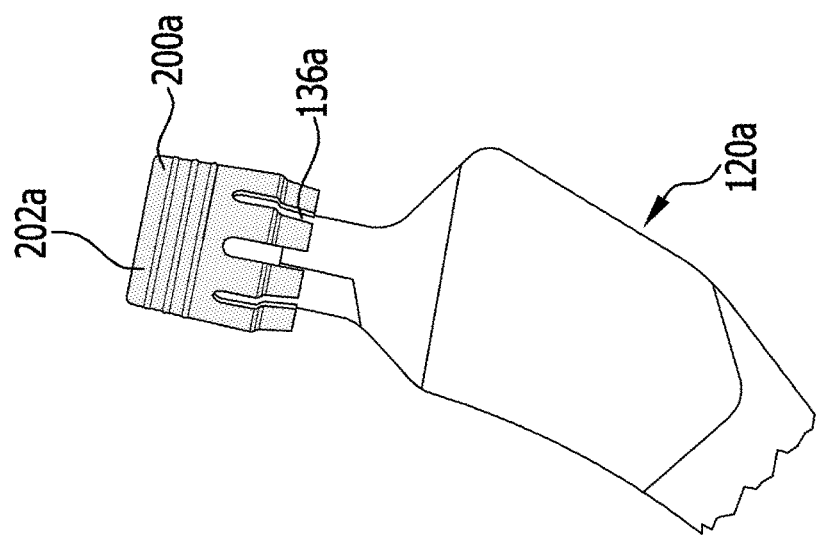
FIG. 5c is a schematic partial view of a hip stem for the indication of coxa valga.
Figure 5B:
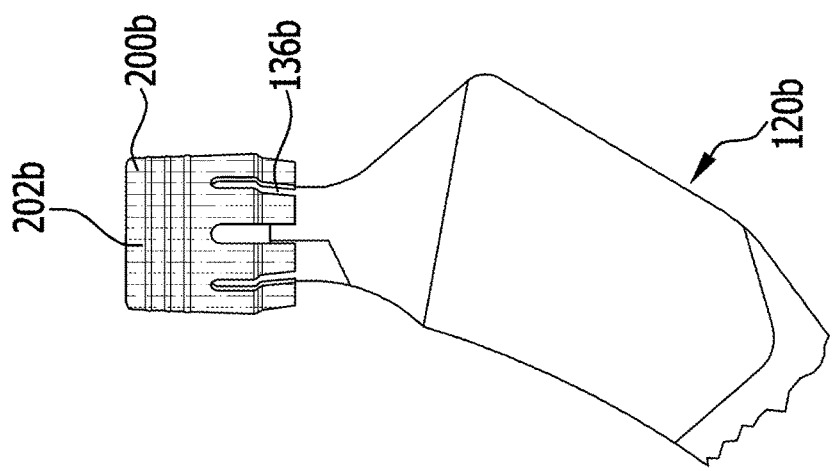
FIG. 5b is a schematic partial view of a hip stem for the indication of coxa norma.
Figure 5A:
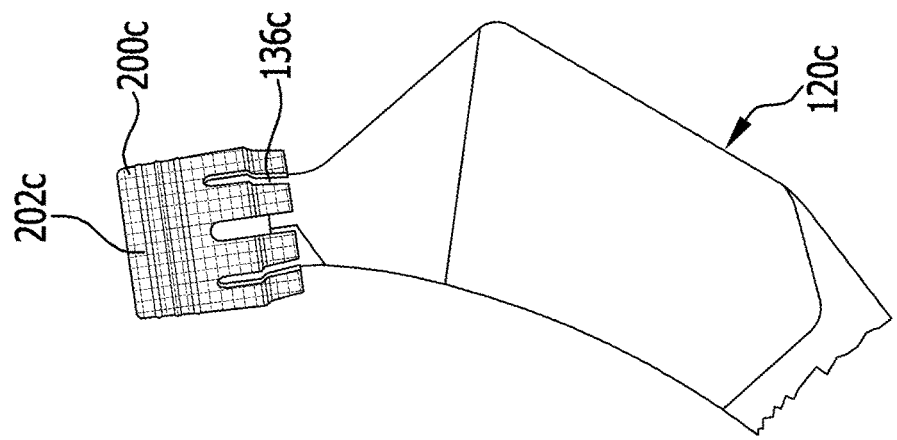
FIG. 5a is a schematic partial view of a hip stem for the indication of coxa vara.

Optionally, as exemplified in FIGS. 5a to 5c, in order to facilitate for a surgeon the preparation of a femur bone, identification elements 200a, 200b and 200c are configured in the form of protective caps 202a, 202b and 202c which are capable of being applied to or temporarily coupled with the necks 136a, 136b and 136c of the prosthesis stems 120a, 120b and 120c.

Optionally, the identification elements 200a, 200b and 200c are coloured in a manner corresponding to the indication for the respective prosthesis stem 120a, 120b and 120c, namely using the same colours that serve to identify the depth stops 152a, 152b and 152c, i.e. for example blue for the indication of coxa vara, orange for the indication of coxa norma and green for the indication of coxa valga. Thus, for example, a surgeon can select the stem 120b corresponding to the indication of coxa norma and will then know immediately that in order to prepare the femur bone optimally for implanting the prosthesis stem 120b he or she must impact the rasp stem 146 thereinto until the depth stop 152b has been reached, the depth stop face 154b of which is coloured in the same colour as that of the identification element 200b.

The protective caps 202a, 202b and 202c can optionally comprise a coupling device that allows force-locking and/or form-locking connection to the necks 136a, 136b and 136c. The protective caps 202a, 202b and 202c serve, on the one hand, to protect the necks 136a, 136b and 136c from damage thereto and, on the other hand, to identify the indication for the respective prosthesis stem 120a, 120b and 120c.

Once the prosthesis stems 120a, 120b and 120c have been inserted, the protective caps 202a, 202b and 202c are removed and a joint head that fits the particular patient is placed onto the necks 136a, 136b and 136c.

FIG. 6 shows a schematic representation of an exemplary implantation set 204 comprising a total of three different implant parts in the form of prosthesis stems 120a', 120b' and 120c'.

The prosthesis stems 120a', 120b' and 120c' differ from the prosthesis stems 120a, 120b and 120c in that they comprise different identification elements 200a', 200b' and 200c'. The identification elements 200a', 200b' and 200c' are arranged on planar end faces 204a', 204b' and 204c' of the necks 136a', 136b' and 136c' pointing in a proximal direction. They are configured in the form of geometrical surface portions 206a', 206b' and 206c', each of which is circular in shape.

The surface portions 206a', 206b' and 206c' in turn are coloured, namely with the same colours as those used for the depth stop faces 154a, 154b and 154c of the rasp stem 146.

If, for example, the surgeon selects the prosthesis stem 120a' for treatment of the coxa valga indication, then he or she needs to impact the rasp stem 146 into the femur bone only until the depth stop 152a has been reached.

The three prosthesis stems 120a', 120b' and 120c' form a modular implant set 206 and together with the rasping instrument 144 form the implantation set 204.

REFERENCE SYMBOL LIST

10a, 10b, 10c femur bone
12 coxa valga
14a, 14b, 14c CCD angle
16 coxa norma
18 coxa vara
20a, 20b, 20c prosthesis stem
22a, 22b, 22c side faces
24 end faces
26a, 26b, 26c centre points
28 longitudinal direction
30 distance
32 distance
34 end
36a, 36b, 36c neck
38 neck longitudinal axis
40a, 40b, 40c femoral head
42 instrumentation
44 rasping instrument
46 rasp stem
48 side faces
50 side faces
52a, 52b, 52c depth stop
54a, 54b, 54c depth stop face
56 plane of symmetry
58a, 58b, 58c depth stop face plane
60a, 60b, 60c width
62a, 62b, 62c end face portions
64 coupling end face
66 coupling element
68 side faces
70 cylindrical surface
72 recess
74 end face
76 coupling element longitudinal axis 78 angle
80 side faces
82 groove
84 edge
86 rasping tooth
88 front face
90 angle
120a, 120b, 120c prosthesis stem
128 longitudinal direction
130 distance
132 distance
136a, 136b, 136c neck
142 instrumentation
144 rasping instrument
146 rasp stem
152a, 152b, 152c depth stop
154a, 154b, 154c depth stop face
156 plane of symmetry
158a, 158b, 158c depth stop face plane
166 coupling element
176 coupling element longitudinal axis
180 side face
186 rasping tooth
192a, 192b groove
194a, 194b groove side faces
196 end face
198a, 198b, 198c shoulder height faces
200a, 200b, 200c identification element
202a, 202b, 202c protective cap
204 implantation set
206 implant set
120a', 120b', 120c' prosthesis stem
200a', 200b', 200c' identification element
204a', 204b', 204c' end face
206a', 206b', 206c' surface portion

What is claimed is:

1. Medical instrumentation for implanting a hip joint stem, comprising:
a rasping instrument having a rasp stem defining a longitudinal direction,
wherein:
the rasp stem has at least two depth stops arranged or formed thereon,
each of the at least two depth stops comprises at least one depth stop face, and
the depth stop faces defined by the at least two depth stops have different surface textures or are differently colored.

2. Medical instrumentation in accordance with claim 1, wherein an end face of the rasp stem pointing in a proximal direction comprises the at least one depth stop face.

3. Medical instrumentation in accordance with claim 1, wherein at least one of the at least two depth stops comprises at least one groove.

4. Medical instrumentation in accordance with claim 3, wherein at least one of:
the at least one groove on the rasp stem extends parallel or essentially parallel to an end face of the rasp stem pointing in a proximal direction or extends transversely to the longitudinal direction, and
the at least one groove at least one of defines a groove longitudinal direction and extends in a straight line or in an essentially straight line.

5. Medical instrumentation in accordance with claim 1, wherein at least two of the at least two depth stops comprise at least one groove.

6. Medical instrumentation in accordance with claim 1, wherein the at least one depth stop face of one of the at least two depth stops at least one of:
is spaced apart from the at least one depth stop face of another one of the at least two depth stops relative to the longitudinal direction, and
extends parallel or essentially parallel to the at least one depth stop face of another one of the at least two depth stops.

7. Medical instrumentation in accordance with claim 1, wherein at least one of:
the rasp stem is of symmetrical or essentially symmetrical configuration with respect to a plane of symmetry which runs transversely to at least one of the depth stop faces, and
three depth stop faces are provided, the three depth stop faces being arranged or formed in equidistant or essentially equidistant relation with respect to the longitudinal direction.

8. Medical instrumentation in accordance with claim 1, wherein the at least one depth stop face is planar.

9. Medical instrumentation for implanting a hip joint stem, comprising:
a rasping instrument having a rasp stem defining a longitudinal direction,
wherein:
the rasp stem has at least two depth stops arranged or formed thereon,
the at least two depth stops are arranged or formed in spaced-apart relationship to each other.

10. Medical instrumentation in accordance with claim 9, wherein each of the at least two depth stops comprises at least one depth stop face.

11. Medical instrumentation in accordance with claim 10, wherein the depth stop faces defined by the at least two depth stops have different surface textures or are differently colored.

12. Medical instrumentation in accordance with claim 10, wherein at least one of the at least two depth stops comprises two depth stop faces.

13. Medical instrumentation in accordance with claim 10, wherein the at least one depth stop face is planar.

14. Medical instrumentation in accordance with claim 10, wherein the at least one depth stop face of one of the at least two depth stops at least one of:
is spaced apart from the at least one depth stop face of another one of the at least two depth stops relative to the longitudinal direction, and
extends parallel or essentially parallel to the at least one depth stop face of another one of the at least two depth stops.

15. Medical instrumentation in accordance with claim 10, wherein at least one of:
the rasp stem has end face portions pointing in a proximal direction, said end face portions forming or comprising the depth stop faces, and
the at least two depth stop faces define depth stop face planes which extend transversely to the longitudinal direction.

16. Medical instrumentation in accordance with claim 10, wherein at least one of:
the rasp stem is of symmetrical or essentially symmetrical configuration with respect to a plane of symmetry which runs transversely to at least one of the depth stop faces, and three depth stop faces are provided, the three depth stop faces being arranged or formed in equidistant or essentially equidistant relation with respect to the longitudinal direction.

17. Medical instrumentation for implanting a hip joint stem, comprising:
a rasping instrument having a rasp stem defining a longitudinal direction,
wherein:
the rasp stem has at least two depth stops arranged or formed thereon,
at least one of the at least two depth stops comprises at least one groove, and
at least one of:
the at least one groove is formed on a side face of the rasp stem that points in a direction transversely to the longitudinal direction, and
the at least one groove comprises at least one groove side face and the at least one groove side face defines at least one depth stop face.

18. Implantation set, comprising;
a modular implant set, comprising at least two different implant parts, and
medical instrumentation for implanting a hip joint stem, comprising a rasping instrument having a rasp stem defining a longitudinal direction,
wherein:
the rasp stem has at least two depth stops arranged or formed thereon,
the at least two different implant parts each comprise an identification element, and
the identification elements of the at least two different implant parts are different from each other at least one of in respect of color schemes of the identification elements, and on the basis of surface textures of the identification elements.

19. Implantation set in accordance with claim 18, wherein each identification element of the at least two different implant parts is associated with one of the at least two depth stops.

20. Implantation set in accordance with claim 18, wherein at least one of:
the identification elements of the at least two different implant parts are configured in the form of geometrical surface portions, and
the identification elements are configured such that they are releasably connectable to the at least two different implant parts or such that they are arranged or formed in a non-releasable relationship therewith.

* * * * *